United States Patent [19]

Lee

[11] Patent Number: 6,010,481
[45] Date of Patent: Jan. 4, 2000

[54] SAFE DISPOSABLE SYRINGE

[76] Inventor: Pi-Chung Lee, No. 610-1, Sec. 7 Chung-Hsiao E. Rd. 4Lin, Chung-Nan Li, Nan-Kang Dist, Taipei, Taiwan

[21] Appl. No.: 09/246,804

[22] Filed: Feb. 9, 1999

[51] Int. Cl.[7] .................................................. A61M 5/00
[52] U.S. Cl. ........................... 604/110; 604/187; 604/240
[58] Field of Search .................................... 604/110, 263, 604/187, 240, 242, 264, 192

[56] References Cited

U.S. PATENT DOCUMENTS

| 5,015,234 | 5/1991 | Jullien ...................................... 604/110 |
| 5,364,370 | 11/1994 | Szerlip et al. ...................... 604/263 X |
| 5,738,220 | 4/1998 | Geszler ............................... 604/263 X |
| 5,743,888 | 4/1998 | Wilkes et al. ....................... 604/192 X |

*Primary Examiner*—John D. Yasko
*Attorney, Agent, or Firm*—Bacon & Thomas

[57] ABSTRACT

A disposable syringe includes a hollow barrel, an annular outer neck and inner neck mounted on the top of the hollow barrel respectively, a first cavity contained in the inner neck and having two opposite abutting edges, a needle located in the inner neck and having a lower end secured in the top of the hollow barrel and an upper end projecting from the inner neck, a rotary cap rotatably mounted on the outer neck and containing a second cavity aligning with the first cavity, a guide slot contained in the top of the rotary cap to receive the needle therein and connecting to the first cavity, and a drive knob pivotally received in the second cavity and having a first end portion containing a needle hole to receive the needle therein, a mediate portion abutting one of the two abutting edges of the first cavity, and a second end portion secured to the rotary cap to rotate therewith.

10 Claims, 6 Drawing Sheets

SAFE DISPOSABLE SYRINGE

CROSS-REFERENCES TO RELATED APPLICATIONS

Not Applicable.

BACKGROUND OF THE INVENTION

1. Field of the Invention

The present invention relates to a safe disposable syringe.

2. Description of the Related Art

A conventional disposable syringe comprises a hollow barrel, and a needle detachably attached to the hollow barrel. The needle needs to be separated from the hollow barrel to dispose of the disposable syringe. However, the needle projecting outward from the hollow barrel tends to puncture the operator during the disposal process. The present invention has arisen to mitigate and/or obviate the disadvantage of the conventional disposable syringe.

BRIEF SUMMARY OF THE INVENTION

In accordance with one aspect of the present invention, there is provided a disposable syringe comprising: a hollow barrel; an annular outer neck mounted on the top of the hollow barrel; an annular inner neck mounted on the top of the hollow barrel, and located in the outer neck, a first cavity transversely contained in the inner neck and having two opposite abutting edges; a needle located in the inner neck and having a lower end secured in the top of the hollow barrel and an upper end projecting from the inner neck; a cylindrical rotary cap rotatably mounted on the outer neck and containing a second cavity transversely defined therein and aligning with the first cavity, an elongated guide slot contained in the top of the rotary cap to receive the needle therein and connecting to the first cavity; and a drive knob pivotally received in the second cavity and having a first end portion containing a needle hole to receive the needle therein, a mediate portion abutting one of the two abutting edges of the first cavity, and a second end portion secured to the rotary cap to rotate therewith.

The rotary cap includes an annular flange extending downward from the bottom thereof and located between the inner neck and the outer neck, and an opening transversely contained in the annular flange and connecting to the second cavity to receive the first end portion of the drive knob therein. The opening includes two opposite abutting edges, and the first end portion of the drive knob abuts one of the two abutting edges of the opening to move therewith.

Further benefits and advantages of the present invention will become apparent after a careful reading of the detailed description with appropriate reference to the accompanying drawings.

DETAILED DESCRIPTION OF THE INVENTION

Figure 1:
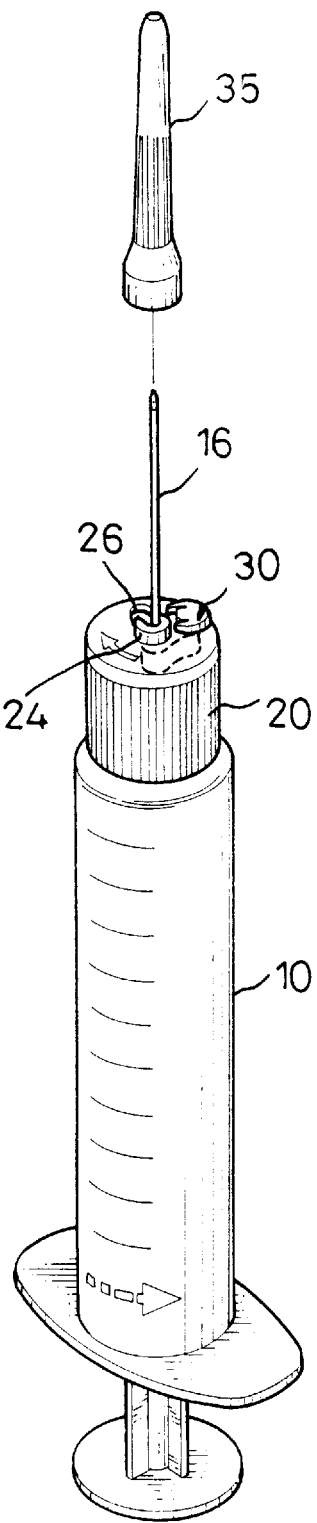
FIG. 1 is a perspective view of a safe disposable syringe in accordance with the present invention.

Referring now to the drawings and initially to FIGS. 1–4, a safe disposable syringe in accordance with the present invention comprises a hollow barrel (10), an annular outer neck (11) mounted on the top of the hollow barrel (10), an annular inner neck (13) mounted on the top of the hollow barrel (10), and located in the outer neck (11), a first cavity (14) transversely contained in the inner neck (13) and having two opposite abutting edges (140), an annular guide groove (18) defined between the inner neck (13) and the outer neck (11) and connecting to the first cavity (14), a positioning column (15) secured on the top of the barrel (10) and located in the inner neck (13), a needle (16) located in the inner neck (13) and having a lower end secured to the positioning column (15) and an upper end projecting from the inner neck (13), a cylindrical rotary cap (20) rotatably mounted on the outer neck (11) and containing a second cavity (27) transversely defined therein and aligning with the first cavity (14), a elongated guide slot (26) contained in the top of the rotary cap (20) to receive the needle (16) therein and connecting to the first cavity (14), and a drive knob (30) pivotally received in the second cavity (27) and having a first end portion containing a needle hole (33) to receive the needle (16) therein, a mediate portion abutting one of the two abutting edges (140) of the first cavity (14), and a second end portion secured to the rotary cap (20) and abutting the wall of the second cavity (27) to rotate therewith.

The outer neck (11) includes a plurality of locking rings (12) formed on the periphery thereof, and the rotary cap (20) includes a plurality of an annular locking grooves (21) each contained in the inner wall thereof and each receiving one of the corresponding locking rings (12) therein, thereby detachably mounting the rotary cap (20) on the outer neck (11).

The rotary cap (20) includes a retaining lug (24) extending outward from the top thereof and containing an opening (25) connecting to the guide slot (26) to receive the needle (16) therein. The disposable syringe comprises an elongated cover (35) detachably mounted on the retaining lug (24) to receive the needle (16) therein.

The drive knob (30) further includes a retaining stub (32) formed on the first end portion thereof and detachably received in the opening (25), a protrusion (31) extending outward from the second end portion thereof and received in the second cavity (27), and a retaining piece (310) extending from the protrusion (31) and abutting the top of the rotary cap (20).

The rotary cap (20) includes an annular flange (22) extending downward from the bottom thereof and located between the inner neck (13) and the outer neck (11), and an opening (23) transversely contained in the annular flange (22) and connecting to the second cavity (27) to receive the first end portion of the drive knob (30) therein. The opening (23) includes two opposite abutting edges (230), and the first end portion of the drive knob (30) abuts one of the two abutting edges (230) of the opening (23) to move therewith.

Figure 2:
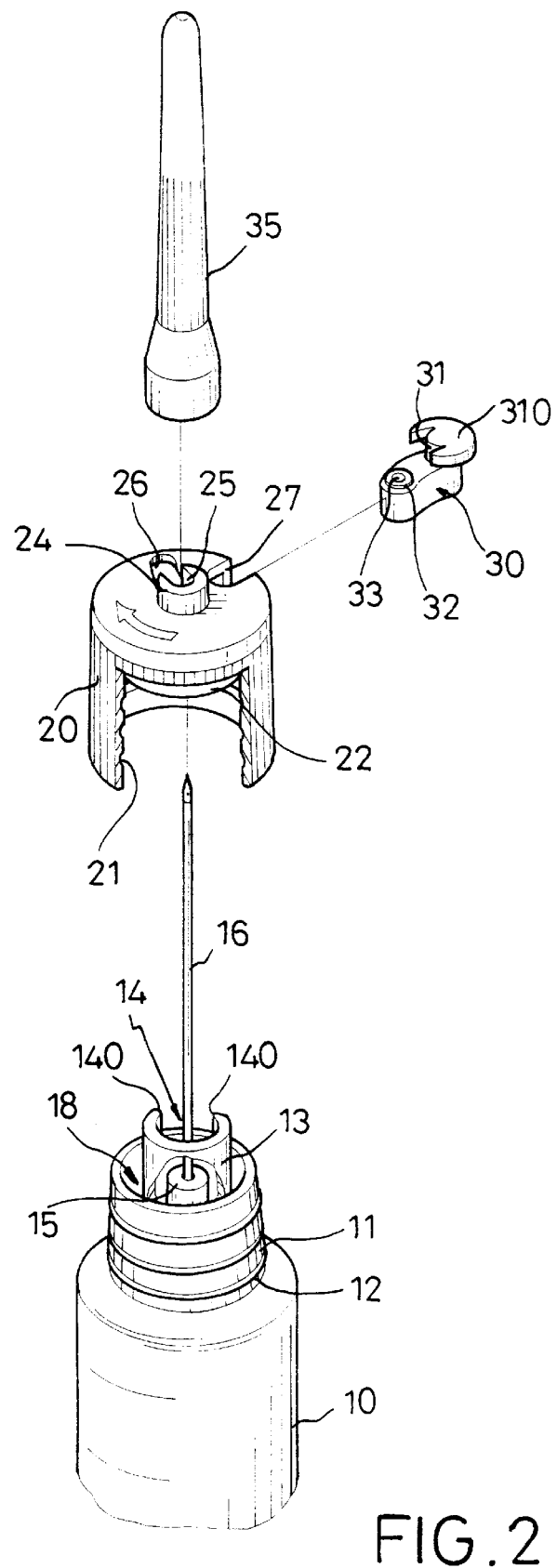
FIG. 2 is an exploded perspective view of the safe disposable syringe as shown in FIG. 1.
Figure 3:
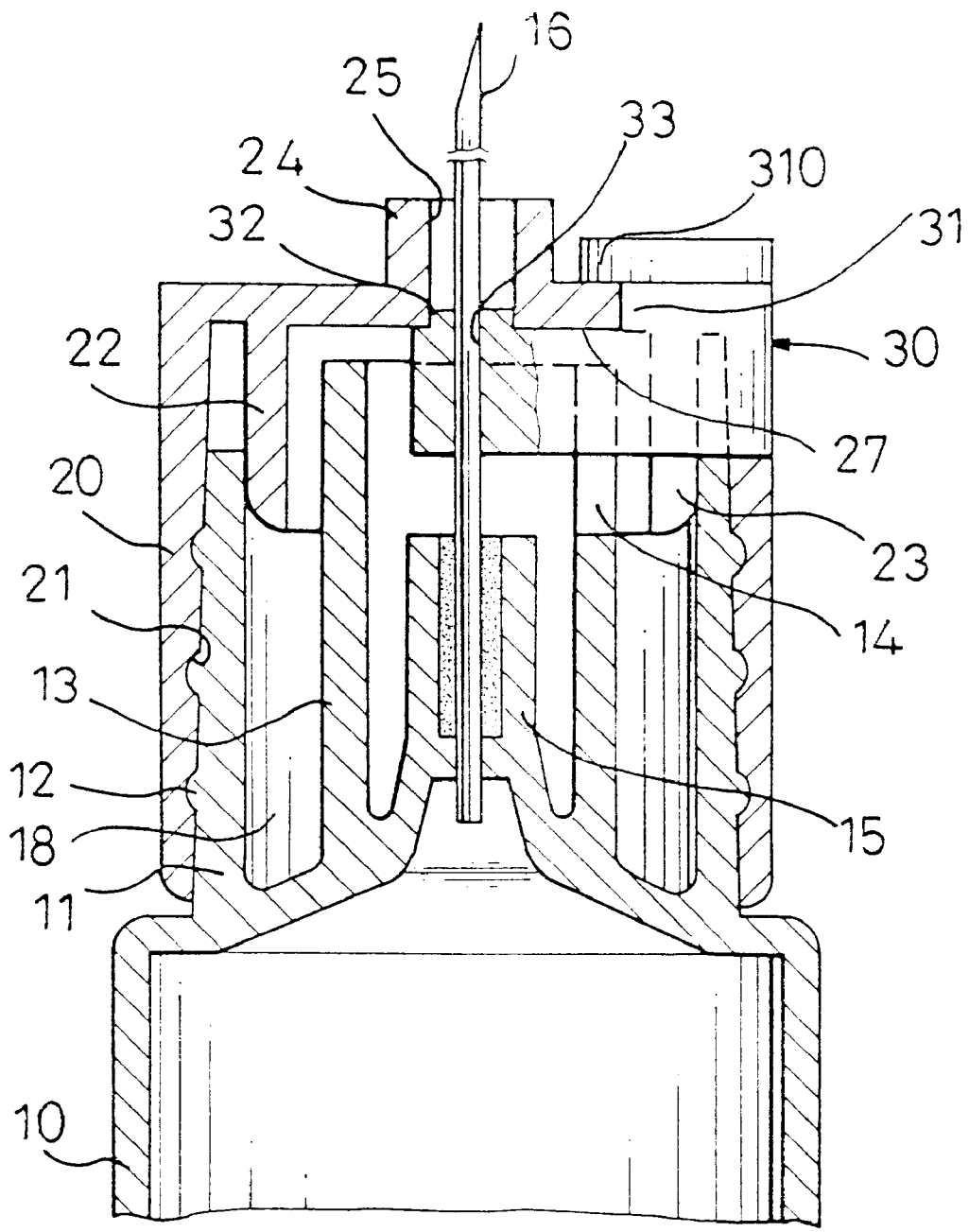
FIG. 3 is a front plan cross-sectional view of the safe disposable syringe as shown in FIG. 1.
Figure 4:
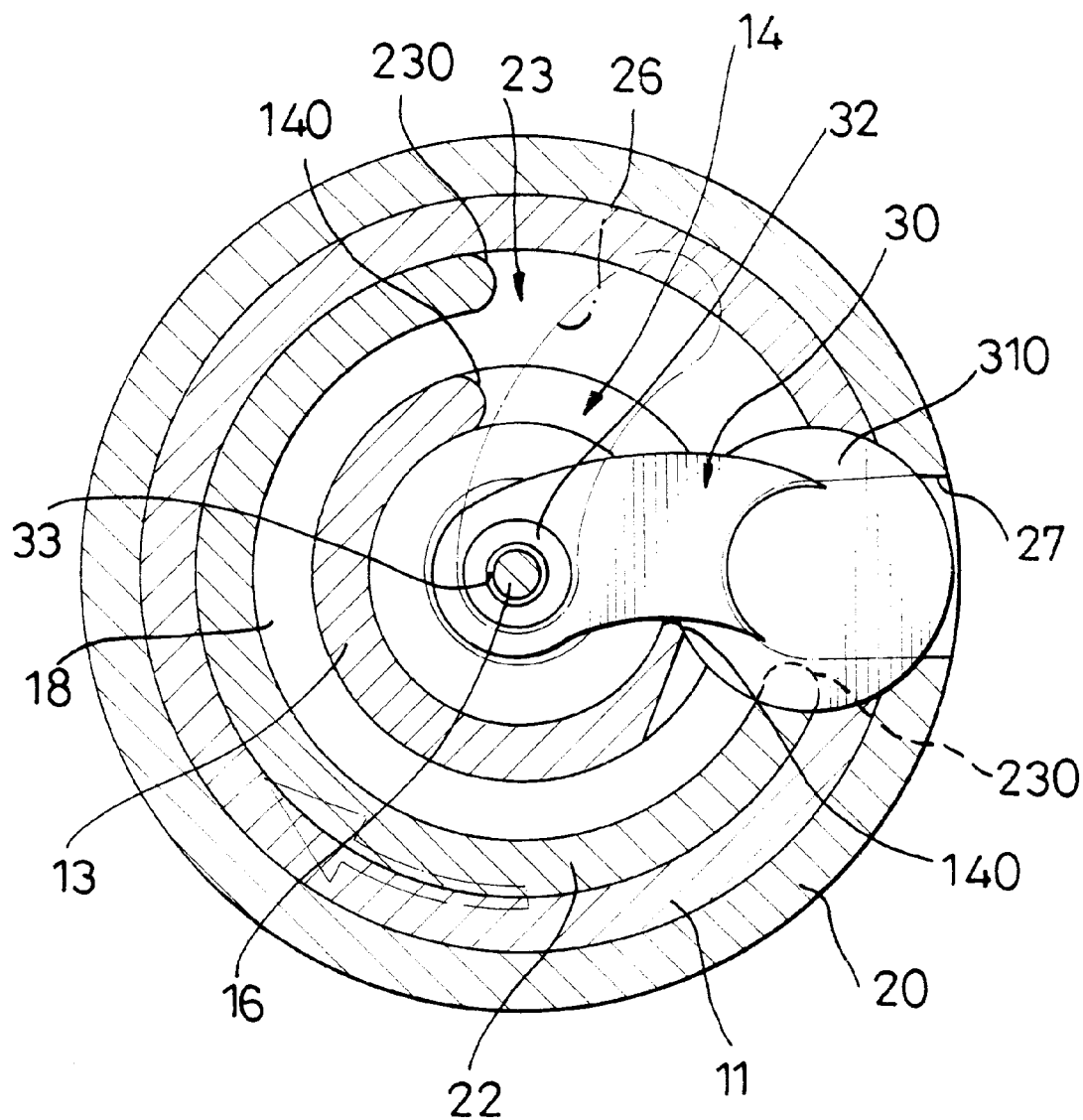
FIG. 4 is a top plan cross-sectional view of the safe disposable syringe as shown in FIG. 1.
Figure 5:
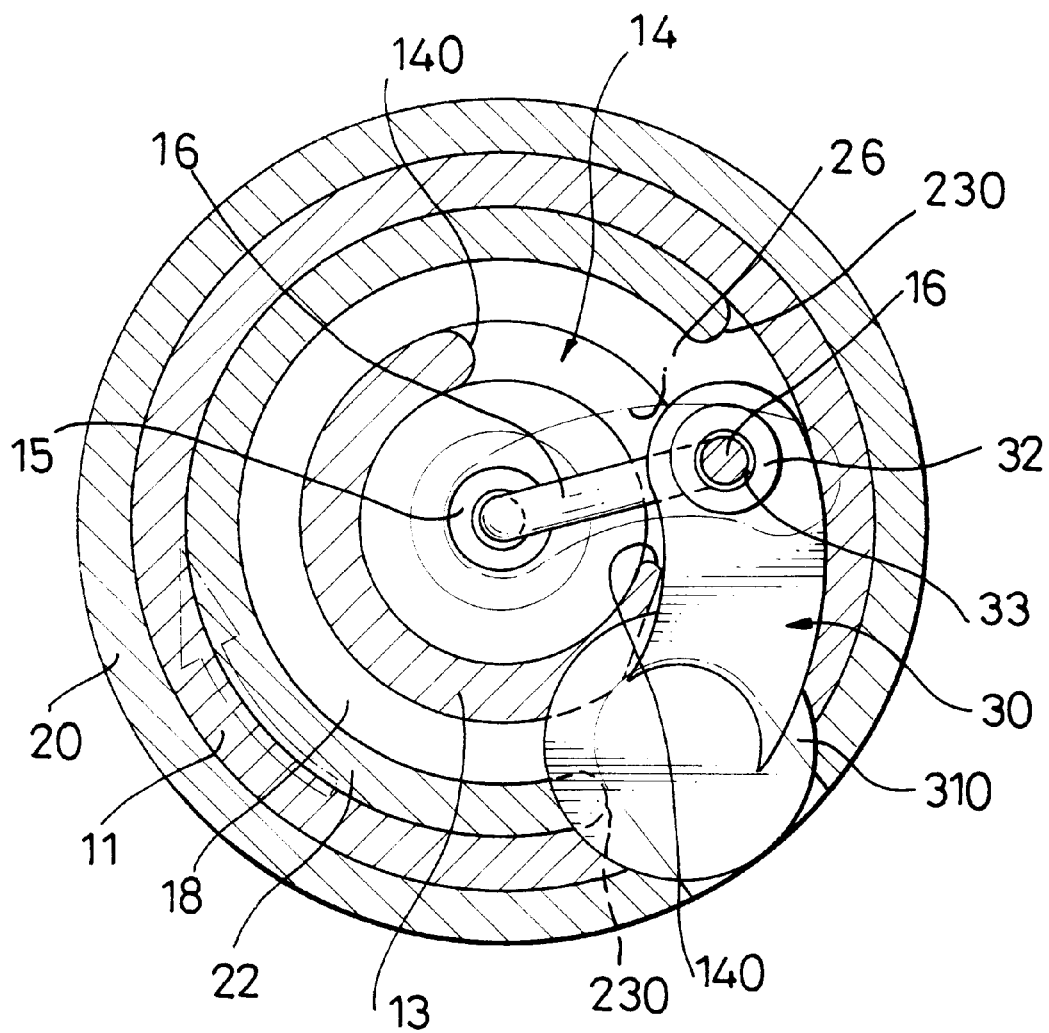
FIG. 5 is an operational view of the safe disposable syringe as shown in FIG. 4.
Figure 6:
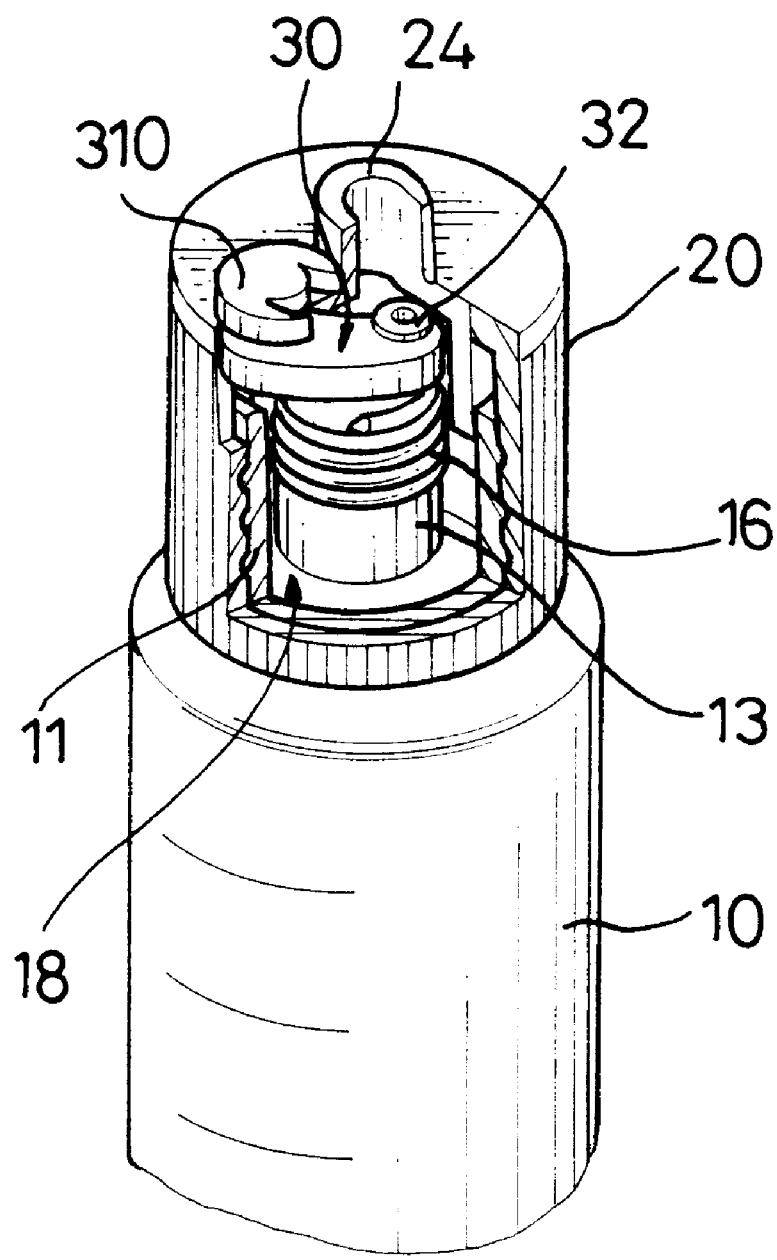
FIG. 6 is a perspective view in partial section of the safe disposable syringe, wherein the needle is retracted into the rotary cap.

In operation, referring to FIGS. 4–6 with reference to FIGS. 1–3, when the intent is to dispose of the safe disposable syringe after it is used, the rotary cap (20) is rotated relative to the outer neck (11) in the direction as indicated by the arrow on top of the cap shown in FIG. 1, thereby pressing the first end portion of the drive knob (30) so as to synchronously move with the rotary cap (20).

At the same time, the mediate portion of the drive knob (30) is fixed by the abutting edge (140) of the first cavity (14) of the inner neck (13) which is fixed during the movement of the first end portion of the drive knob (30) such that the drive knob (30) is pivoted relative to the abutting edge (140) from the position as shown in FIG. 4 to the position as shown in FIG. 5, thereby deviating the upper end of the needle (16) through the guide slot (26) by means of the needle hole (33) of the retaining stub (32) of the second end portion of the drive knob (30) to the position as shown in FIG. 5, so as to guide the upper end of the needle (16) into the guide groove (18) such that the upper end of the needle (16) can be wound around the outer wall of the inner neck (13).

The rotary cap (20) is continuously rotated relative to the outer neck (11) such that the needle (16) can be wound around the outer wall of the inner neck (13) as shown in FIG. 6 and securely received in the guide groove (18), thereby retracting the needle (16) into the rotary cap (20). In such a manner, the needle (16) is entirely retracted into the rotary cap (20) when the intent is to dispose of the disposable syringe, thereby preventing the needle (16) from puncturing the operator during the disposal process.

It should be clear to those skilled in the art that further embodiments may be made without departing from the scope and spirit of the present invention.

What is claimed is:

1. A disposable syringe comprising:

a hollow barrel (10);

an annular outer neck (11) mounted on the top of said hollow barrel (10);

an annular inner neck (13) mounted on the top of said hollow barrel (10), and located in said outer neck (11), a first cavity (14) transversely contained in said inner neck (13) and having two opposite abutting edges (140);

a needle (16) located in said inner neck (13) and having a lower end secured in the top of said hollow barrel (10) and an upper end extending outward from said inner neck (13);

a cylindrical rotary cap (20) rotatably mounted on said outer neck (11) and containing a second cavity (27) transversely defined therein and aligning with said first cavity (14), an elongated guide slot (26) contained in the top of said rotary cap (20) to receive said needle (16) therein and connecting to said first cavity (14); and a drive knob (30) pivotally received in said second cavity (27) and having a first end portion containing a needle hole (33) to receive said needle (16) therein, a mediate portion abutting one of said two abutting edges (140) of said first cavity (14), and a second end portion secured to said rotary cap (20) to rotate therewith.

2. The disposable syringe in accordance with claim 1, further comprising an annular guide groove (18) defined between said inner neck (13) and said outer neck (11) and connecting to said first cavity (14).

3. The disposable syringe in accordance with claim 1, wherein said outer neck (11) includes a plurality of locking rings (12) formed on the periphery thereof, and said rotary cap (20) includes a plurality of an annular locking grooves (21) each contained in the inner wall thereof and each receiving one of said corresponding locking rings (12) therein.

4. The disposable syringe in accordance with claim 1, further comprising a positioning column (15) secured on the top of said barrel (10) and located in said inner neck (13), wherein said needle (16) is secured to said positioning column (15) at the lower end portion thereof.

5. The disposable syringe in accordance with claim 1, wherein said rotary cap (20) includes a retaining lug (24) extending outward from the top thereof and containing an opening (25) connecting to said guide slot (26) to receive said needle (16) therein.

6. The disposable syringe in accordance with claim 5, wherein said drive knob (30) includes a retaining stub (32) formed on the first end portion thereof and detachably received in said opening (25).

7. The disposable syringe in accordance with claim 5, further comprising an elongated cover (35) detachably mounted on said retaining lug (24) to receive said needle (16) therein.

8. The disposable syringe in accordance with claim 1, wherein said drive knob (30) includes a protrusion (31) projecting from the second end portion thereof and received in said second cavity (27), and a retaining piece (310) extending from said protrusion (31) and abutting the top of said rotary cap (20).

9. The disposable syringe in accordance with claim 1, wherein said rotary cap (20) includes an annular flange (22) extending downward from the bottom thereof and located between said inner neck (13) and said outer neck (11), and an opening (23) transversely contained in said annular flange (22) and connecting to said second cavity (27) to receive said first end portion of said drive knob (30) therein.

10. The disposable syringe in accordance with claim 9, wherein said opening (23) includes two opposite abutting edges (230), and said first end portion of said drive knob (30) abuts one of said two abutting edges (230) of said opening (23) to move therewith.

* * * * *